United States Patent [19]

Müller et al.

[11] 4,419,244

[45] Dec. 6, 1983

[54] METHOD AND ARRANGEMENT FOR AERATION OF LIQUIDS

[75] Inventors: Hans Müller, Erlenbach; Felix Müller, Staefa, both of Switzerland

[73] Assignee: Chemap AG, Männedorf, Switzerland

[21] Appl. No.: 329,567

[22] Filed: Dec. 10, 1981

Related U.S. Application Data

[63] Continuation-in-part of Ser. No. 81,450, Oct. 3, 1979, abandoned.

[30] Foreign Application Priority Data

Oct. 10, 1978 [CH] Switzerland ............... 10503/78

[51] Int. Cl.³ .............. C02F 3/20; C12M 1/06; C12M 1/08
[52] U.S. Cl. ............................. 210/629; 210/194; 210/199; 261/87; 261/93; 435/314; 435/315
[58] Field of Search .......... 210/218, 220, 221.1, 210/221.2, 621, 629, 194, 205, 208, 628, 620, 199; 261/93, 87, 36 R, DIG. 75; 435/313-315, 243, 244

[56] References Cited

U.S. PATENT DOCUMENTS

| | | | |
|---|---|---|---|
| 2,944,802 | 7/1960 | Daman | 261/93 |
| 3,409,130 | 11/1968 | Nakamura | 261/93 |
| 3,813,086 | 5/1974 | Ebner et al. | 261/93 |
| 3,904,393 | 9/1975 | Morse | 261/DIG. 75 |
| 4,029,724 | 6/1977 | Müller et al. | 435/314 |
| 4,073,696 | 2/1978 | Müller | 261/93 |
| 4,078,026 | 3/1978 | Fallenius | 261/93 |
| 4,283,357 | 8/1981 | Sidery | 261/87 |

FOREIGN PATENT DOCUMENTS 9852  4/1980  European Pat. Off. .
819785  9/1959  United Kingdom .......... 261/93

*Primary Examiner*—Benoît Castel
*Attorney, Agent, or Firm*—Michael J. Striker

[57] ABSTRACT

A method of aerating liquids, particularly for aerobic growing of microorganisms, has the steps of forming a circumferential stream of liquid, forming a longitudinal stream of liquid, and superimposing these streams so as to form a combined closed spiral-shaped stream. An arrangement is provided in which the circumferential stream is formed by an upright conduit tube and an impeller, the longitudinal stream is formed by a distributing element with a plurality of nozzles, and the superimposing of the streams is attained by fixedly mounting the distributing element relative to the impeller.

7 Claims, 7 Drawing Figures

4,419,244

METHOD AND ARRANGEMENT FOR AERATION OF LIQUIDS

CROSS-REFERENCE TO A RELATED APPLICATION

This application is a continuation-in-part of application Ser. No. 81,450, filed Oct. 3, 1979, now abandoned.

BACKGROUND OF THE INVENTION

The present invention relates to a method and arrangement for aeration of liquids, particularly for aerobic growing of microorganisms.

Methods and arrangements for aeration in the processes of growing microorganisms are known in the art. Agitating devices or stirrers with an upper drive and a lower drive have been found suitable for rotation of liquid volumes of up to 300 m$^3$. For rotation of larger liquid volumes in closed containers air is supplied through the bottom of the containers under pressure. Thereby, rotation of the container contents, in accordance with the principle of the air-lift-pump is performed. The known methods and arrangements possess the disadvantages in that in the case of large volumes the mechanical agitation by agitating devices results not only in high energy consumption but also in that the upper drive devices require very long shaft, and the lower drive devices cause sealing problems because of high hydrostatic pressure. When fermenters operating in accordance with the air-lift-pump principle are utilized, it is necessary to provide compressors of great sizes in order to supply compressed air. By no means, however, the homogeneity can be guaranteed in large liquid volumes.

The Swiss Pat. No. 572,978 discloses an arrangement which has a horizontally located container including several rotary devices which are connected with each other in series. Each block forms a unit in a common container. This fermenter is satisfactory with respect to withdrawal of heat, however, it has the disadvantage in that dead zones take place in the regions of not exactly defined limiting faces between two neighboring aeration units.

SUMMARY OF THE INVENTION

Accordingly, it is an object of the present invention to provide a method and an arrangement for aerating liquids, which avoid the disadvantages of the prior art.

More particularly, it is an object of the present invention to provide a method and an arrangement in accordance with which a high homogeneity is guaranteed in large fermenters.

In keeping with these objects and with others which will become apparent hereinafter, one feature of the present invention resides, briefly stated in a method in which a circumferential stream of liquid and a longitudinal stream of liquid are formed in a container and these streams are superimposed so as to form a combined spiral-shaped stream. The invention is also embodied in an arrangement which has means for forming the circumferential stream and the longitudinal stream of liquid, and means for superimposing these streams so as to form the combined spiral-shaped stream.

When the method is performed and the arrangement is constructed in accordance with the present invention a controllable spiral-shaped stream is formed in the reactor, the stream being closed and providing for optimum aeration of the liquid and the microorganisms to be cultivated.

In accordance with an especially advantageous feature of the present invention, the inventive arrangement is formed as a container which is composed of one or several aeration units each provided with the above-mentioned forming and superimposing means and adapted to be mechanically assembled with each other. The ends of this container are closed by semi-spherical walls.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

DESCRIPTION OF A PREFERRED EMBODIMENT

Figure 1:
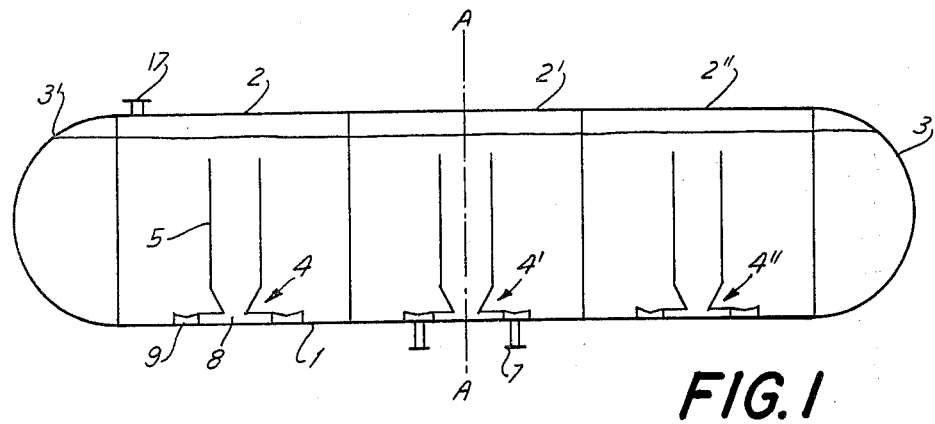
FIG. 1 is a view showing a longitudinal section of an inventive arrangement with three aeration units which can be mechanically assembled with each other.

FIG. 1 shows in its entirety a pressure container having, for example, three aeration units 2, 2' and 2" which can be assembled in accordance with mechanical assembly technique and have, for example, identical diameters and lengths. The pressure container is formed as a tank 1 which is closed at its both ends by semi-spherical end portions 3 and 3'.

Figure 2:
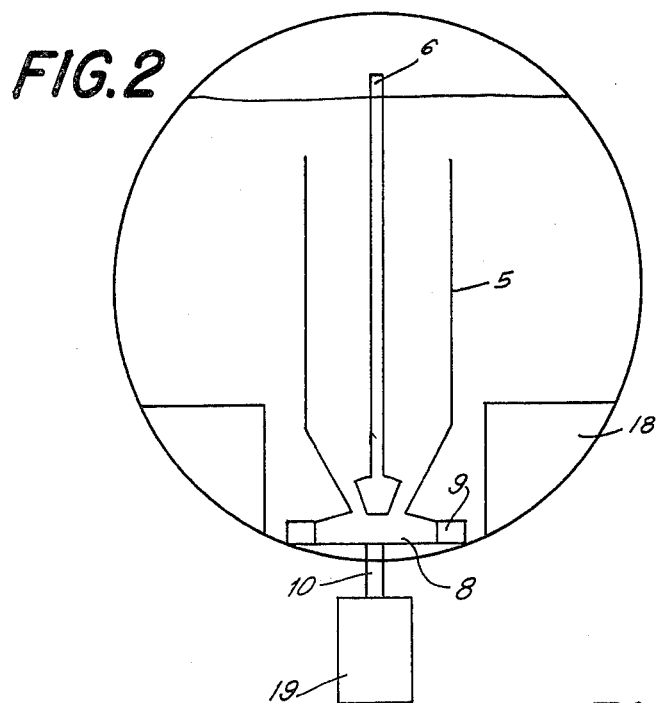
FIG. 2 is a view showing a section taken along line A—A of FIG. 1.

Each aeration unit has an aerating arrangement 4, 4' and 4", respectively. Each aeration arrangement, in turn, is composed of a conduit tube 5, an inner air supply tube 6, a stationary distributor 9, an outer air supply tube 7, and a rotatable pump wheel or impeller 8. As can be seen from FIG. 2, cooling units 18 are movably arranged in the tank 1.

Figure 3:
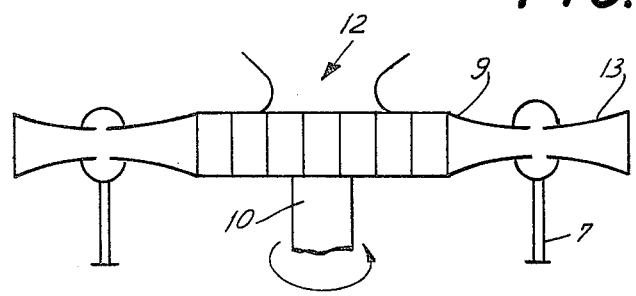
FIG. 3 is a view showing a section taken through a pump unit with a distributor.
Figure 4:
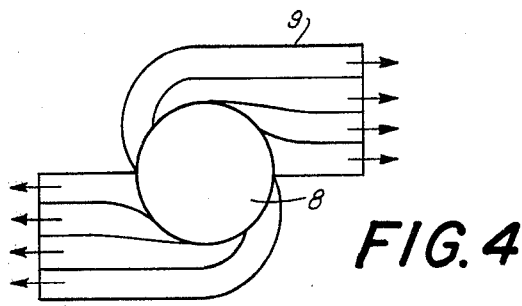
FIG. 4 is a plan view of the pump unit with the distributor.

FIG. 3 depicts the rotatable pump wheel or impeller 8 in detail. The pump wheel 8 is provided with a shaft 10 connected with a rotary drive 19. The pump wheel 8 has at its upper side an inlet opening 12 for the liquid which is aspirated through the conduit tube 5. The distributor 9 is arranged in conventional manner on the bottom of the tank 1 and is stationary. More particularly, it is fixedly mounted on the bottom of the tank 1. This mounting can be performed by any conventional mounting elements which are not shown in the drawing. The distributor 9 is composed of several parallel tubes 13. As shown in FIG. 4, the tubes 13 have openings which are open in opposite directions. FIG. 4 shows a plan view of the distributor 9 associated with the pump wheel 8.

Figure 5:
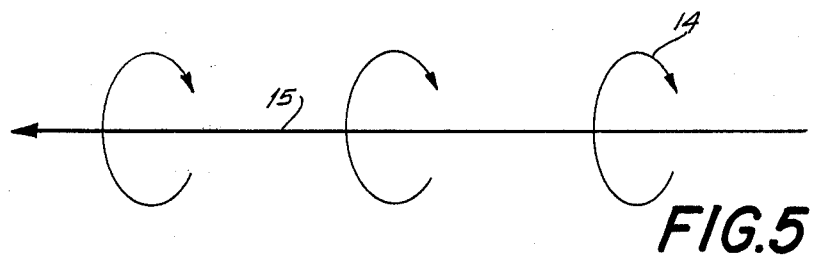
FIGS. 5—7 are views showing liquid stream patterns.
Figure 6:
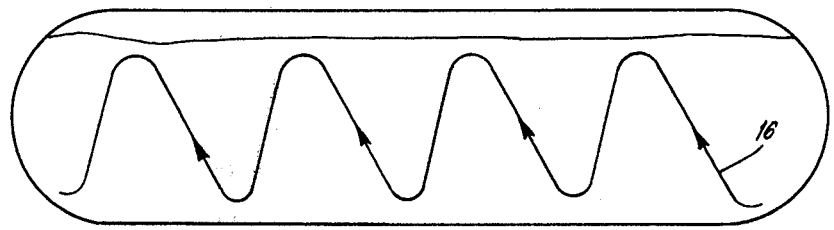
Figure 7:
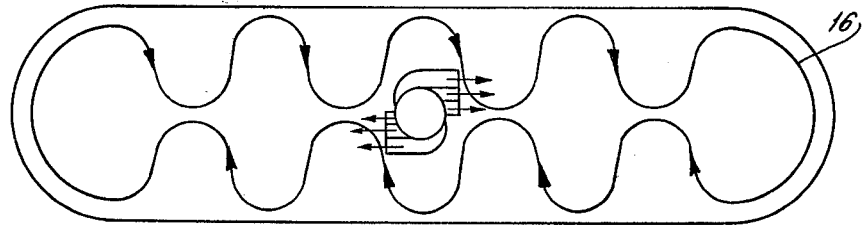

In operation, the rotatable pump wheel 8 rotates relative to the stationary distributor 9. FIG. 5 shows flow pattern of an individual stream produced thereby. As a result of the axial aspiration through the conduit pipe 5 toward the pump wheel 8 and the radial centrifuging, a circumferential stream component 14 is first generated by the rotatable pump wheel 8. The stream component 14 is directed from above downwardly and causes a rotation. A lateral or longitudinal stream 15 is generated by the numerous tubes 13 of the stationary distributor 9 which have outlets identified in FIG. 4 by the arrows. The streams 14 and 15 together form a combined closed spiral stream 16 shown in FIGS. 6 and 7. FIG. 6 is an elevational view and FIG. 7 is a plan view of the container in which the combined stream 16 is formed.

The container is filled with a liquid or a liquid nutrient matter to substantially ⅔ of its volume. For example, with identical relation of the diameter and length, the following filling heights are obtained.

50 m³
100 m³
200 m³
2.261 m
2.84 m
3.58 m

The necessary hydrostatic pressure may be provided by a naturally aspirating turbine. Five individual units each having a volume of 200 m³ is required, for example, for a fermenter having a volume of 1000 m³. Despite the large volumes, the filling height amounts to only 3.58 m.

The pump wheel 8 which is driven, for example, by a not shown electric motor, aspirates liquid through the conduit tube 5. Simultaneously, air is aspirated from the gas space through the inner air supply tube 6. This internal aeration leads to an increased utilization of oxygen in the aerating air. The fresh air can be supplied into the distributor 9 in conventional manner through the driving shaft 10 which is formed hollow and/or the outer air supply tube 7. The spent air is withdrawn through a pipe 17 directly or with interposition of a not shown mechanical foam-breaking device in the container.

The conduits for supply and withdrawal of the fluid to be aerated can be arranged at any point in the lower part of the container. They must preferably be spaced as far as possible from one another. Via the distributor 9, fresh air with a pressure of approximately 3 bar is introduced through nozzles into the most narrow point of the Venturi opening. Simultaneously, air which contains at least 10% of oxygen is aspirated from a head chamber of the fermentor. Thereby, it is possible to increase the utilization of oxygen.

It will be understood that each of the elements described above, or two or more together, may also find a useful application in other types of constructions differing from the types described above.

While the invention has been illustrated and described as embodied in a method and an arrangement for aerating liquid for growing of microorganisms, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method of aerating liquids for aerobic growing of micoorganisms, in an elongated container extending in a substantially horizontal direction and containing a liquid, said container having a plurality of liquid-filled zones arranged adjacent to one another in direction of elongation of said container, the method comprising the steps of: providing a plurality of means each located in each of said zones for forming in each of said zones a longitudinally advancing stream of the liquid accommodated in said container, wherein each of said means for forming a longitudinal stream includes a stationary distributing element mounted on a container bottom and arranged to exit the liquid in the direction of elongation of said container, and a conduit provided for each distributing element for supplying air; providing a plurality of means each located in each of said zones for forming in each of said zones a circumferentially advancing stream of the liquid accommodated in said container, wherein each of said means for forming a circumferential stream of liquid includes a substantially upright conduit tube and an impeller communicating with the same and rotatable about a substantially upright axis so as to form said circumferential stream; and arranging said distributing element of each said means for forming said longitudinal stream to surround said impeller of each of said means for forming said circumferential stream so that said rotatable impeller rotates relative to said stationary distributing element, so as to cause superposition of said circumferential stream and said longitudinal stream in each of said zones and to form a composite closed spiral-shaped stream of liquid in said container travelling in the direction of elongation of said container through all said zones over substantially the entire length of said container.

2. An arrangement for aerating liquids for aerobic growing of micoorganisms, comprising an elongated container extending in a substantially horizontal direction and containing a liquid, said container having a plurality of zones arranged adjacent to one another in direction of elongation of said container; a plurality of means each located in each of said zones for forming in each of said zones a longitudinally advancing stream of the liquid accommodated in said container, each of said means for forming a longitudinal stream including a stationary distributing element mounted on a container bottom and arranged to exit the liquid in the direction of elongation of said container, and a conduit provided for each distributing element for supplying air; and a plurality of means each located in each of said zones for forming in each of said zones a circumferentially advancing stream of the liquid accommodated in said container, each of said means for forming a circumferential stream of liquid including a substantially upright conduit tube and an impeller communicating with the same and rotatable about a substantially upright axis so as to form said circumferential stream, said distributing element of each of said means for forming said longitudinal stream surrounding said impeller of each of said means for forming said circumferential stream so that said rotatable impeller rotates relative to said stationary distributing element, so as to cause superposition of said circumferential stream and said longitudinal stream in each of said zones and to form a composite closed spiral-shaped stream of liquid in said container travelling in the direction of elongation of said container through all said zones over substantially the entire length of said container.

3. An arrangement as defined in claim 2, wherein said container has a longitudinal axis, said distributing element being arranged to direct the liquid in two mutually opposite directions substantially parallel to said longitudinal axis of said container.

4. An arrangement as defined in claim 3, wherein said distributing element is provided with two groups of nozzles, each extending and being open in a respective one of said two mutually opposite directions.

5. An arrangement as defined in claim 2, wherein said container is composed of a plurality of aeration units which are mechanically assembled with each other and each is located in a respective one of said zones and has said circumferential stream forming means and said longitudinal stream forming means so located.

6. An arrangement as defined in claim 5, wherein said aeration units are located adjacent to each other in the direction of elongation of the container, said container having two ends which are spaced from one another in said direction of elongation and closed by semi-spherical walls.

7. An arrangement as defined in claim 5, wherein each of said aeration units has a diameter and a length which relate to one another as 1:1.

* * * * *